United States Patent [19]

Ranger et al.

[11] 4,161,191
[45] Jul. 17, 1979

[54] ADAPTOR FOR CONNECTION TO A FAUCET

[75] Inventors: Anton Ranger, Bruckmühl; Alexander Uebel, Gauting, both of Fed. Rep. of Germany

[73] Assignee: Knorr-Bremse-Bowles-Fluidics GmbH, Munich, Fed. Rep. of Germany

[21] Appl. No.: 737,477

[22] Filed: Nov. 1, 1976

[30] Foreign Application Priority Data

Nov. 6, 1975 [DE] Fed. Rep. of Germany ....... 2549872
Aug. 2, 1976 [DE] Fed. Rep. of Germany ....... 2634721

[51] Int. Cl.² ............................................. F16K 11/06
[52] U.S. Cl. ................................. 137/625.46; 251/352
[58] Field of Search ........... 137/876, 801, 887, 625.46; 251/352, 175

[56] References Cited

U.S. PATENT DOCUMENTS

| 169,988 | 11/1875 | Goodell | 251/352 X |
|---|---|---|---|
| 2,474,286 | 6/1949 | Snyder | 137/876 X |
| 2,521,490 | 9/1950 | Strauss | 251/352 X |
| 3,104,674 | 9/1963 | Bills et al. | 137/625.46 X |
| 3,329,167 | 7/1967 | Boettcher et al. | 137/625.46 |
| 3,444,890 | 5/1969 | Ralston | 137/625.46 X |

FOREIGN PATENT DOCUMENTS 341774  11/1959  Switzerland ........................ 137/625.46

*Primary Examiner*—Arnold Rosenthal
*Attorney, Agent, or Firm*—W. G. Fasse; W. W. Roberts

[57] ABSTRACT

An adapter for connection to a liquid faucet comprises an inlet member, a coaxial outlet member, and a valve device which is rotatable relative to the outlet member about an axis common to the inlet and outlet members. The inlet member is connectable to the outlet end of the liquid faucet. The outlet member has several outlet openings or groups of outlet openings separated from each other. The valve device is rotated in order to continuously adjust the opening ratio between the various outlet openings of the outlet member relative to each other, thereby providing a precisely regulated amount of liquid which is branched off from the liquid faucet for operating auxiliary devices such as a douche.

14 Claims, 5 Drawing Figures

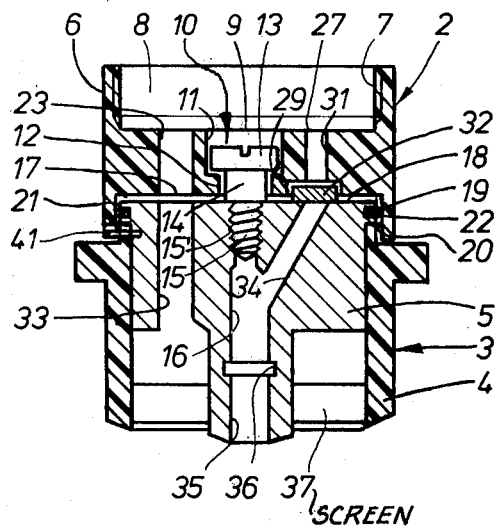
Fig.: 1
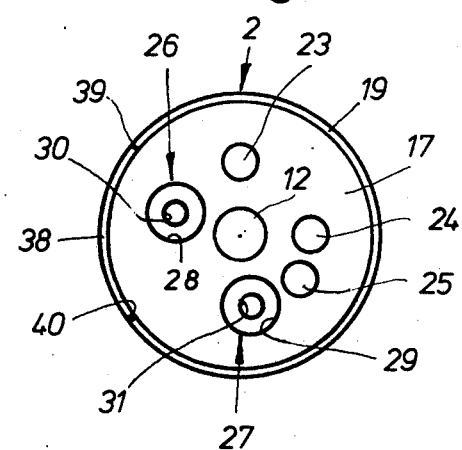
Fig.: 2
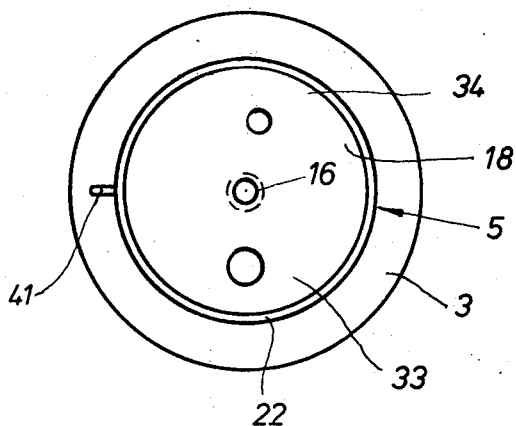
Fig.: 3

Fig.: 4
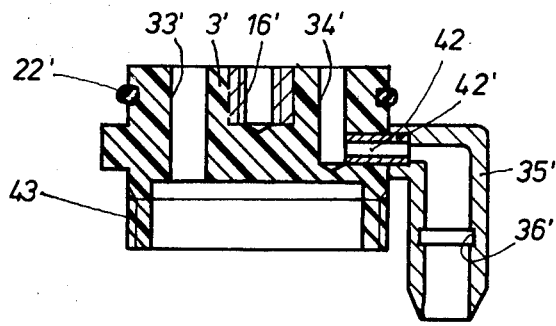
Fig.: 5
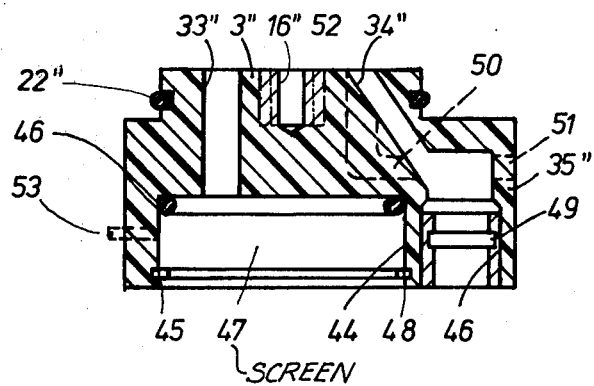

ADAPTOR FOR CONNECTION TO A FAUCET

BACKGROUND OF THE INVENTION

The invention relates to an adapter for connection to a liquid faucet. It involves in particular an adapter for connecting mouth- or skin-massaging douches or skin cleaning douches to conventional water faucets.

Adapters can be used wherever a definite, adjustable amount of liquid is to be branched off from a liquid line for operating apparatus connected thereto, particularly a mouth and/or skin massaging douche or a skin cleaning douche. Such adapters comprising three-way valves should be readily connectable without special aids, particularly to the end of a water faucet. The three-way valves for choosing the amount of liquid to be branched off should be designed here so that they can easily be adjusted by hand with great sensitivity.

For such purposes, an adapter which can be connected to a water faucet and which has a central inlet canal at its connection end, has already been proposed. The inlet canal is connected to a valve bore hole which goes through the adapter in the transversal direction. A three-way slider is guided, axially movably, within the valve bore hole. A main discharge canal branches off from the valve bore hole. The discharge canal is connected to the outlet end of the adapter and, at a distance from this canal, another, secondary canal which leads to a connector laterally disposed at the adapter for the detachable connection to a hose which can be connected to a mouth- and/or skin-massaging douche or a skin cleaning douche. The connection is designed as a pluggable coupling which receives a coupling plug, to which one end of the hose is attached.

The design of the known water connection is already very simple. The handling of the three-way valve for switching the appliance is not complicated. The coupling plug is easily inserted into the pluggable coupling and removed after use. The water connection can furthermore be screwed easily to any conventional water faucet. In this manner, mouth- and/or skin-massaging douches or skin cleaning douches, for instance, can already be used without any auxiliary devices in any household.

In the known adapter, the shifting or switch-over of the three-way valve is accomplished by means of a slider, which can be moved by hand between two end positions. In the one end position of the slider, the connection serves accordingly as an ordinary outlet for a water faucet, while in the other end position of the slider, water flows from the water faucet into the connected line via the pluggable coupling. In the intermediate positions of the slider, the size of the connecting cross section between the faucet and the pluggable coupling can be chosen.

In this known adapter, however, certain difficulties are encountered, inasmuch as the required sealing rings in the three-way slider always slide or rub over the edges of the openings of the main and the secondary canal when it is switched from its one end position to the other one. This causes a relatively heavy stress on the sealing rings. In order to minimize the wear of the sealing rings, the edges of the openings of the canals must not have too sharp edges. Finally, fine regulation of the amount of liquid to be branched off by means of the three-way slider takes a special skill on the part of the user. Also, the three-way slider must be carefully guided in the valve housing and it must be sufficiently hard to operate the slide.

It is therefore an object of the invention to describe an adapter of the type mentioned at the outset which avoids, in particular, the above mentioned wear problems at the valve seals and can also be produced substantially less expensively, and which, in addition, can easily be adjusted by hand with great sensitivity.

SUMMARY OF THE INVENTION

According to the invention, the adapter comprises an inlet part, an outlet part disposed coaxially to the inlet part, and a valve device which is arranged rotatably about the common axis relative to the outlet part between the two parts; the inlet part comprises a device by which it can be connected to the outlet end of the liquid faucet; the outlet end has several outlet openings separated from each other; within the range of rotation, the inlet part is connected, in cooperation with the valve device, either only to one or to several first outlet openings or only to one or several second outlet openings or partly to the first outlet opening or openings and the second outlet opening or openings, the respective opening ratio between the first and and the second connection openings being continuously adjustable by the relative rotation of the valve device with respect to the outlet part.

Further advantageous embodiments and developments according to the invention follow, alone or in conjunction with the main claim, from the features of the subclaims and/or the following description of embodiment examples, particularly for connecting mouth douches.

BRIEF FIGURE DESCRIPTION

In order that the invention may be clearly understood, it will now be described, by way of example, with reference to the accompanying drawings, wherein: The examples are shown, enlarged and schematically, in the attached drawings. There is shown in:

FIG. 1 an axial section through an adapter of the invention in accordance with a first example embodiment;

FIG. 2 a top view onto a part of the adapter according to FIG. 1;

FIG. 3 a top view onto another adapter according to FIG. 1;

FIG. 4 an adapter according to FIG. 1 in a modified embodiment; and in

FIG. 5 an adapter according to FIG. 1 in a still further modified embodiment.

DETAILED DESCRIPTION OF PREFERRED EMBODIMENTS

An adapter according to the invention as per FIG. 1 is screwed to an ordinary water faucet, not shown.

The adapter 1 comprises an inlet part or member 2 and an outlet part or member 3. The outlet part, in turn, comprises an outer sleeve 4 and an inner part 5 which is held in the sleeve 4 secure against rotation. However, the parts 4 and 5 may also be made of one piece.

On the inlet side, the inlet part has a threaded neck 6 with internal thread 7 for connection to the external thread at the end of a water faucet, not shown. The threaded neck 6 may be provided at the same time with an external thread for connection to internal threads of water faucets, so that the inlet part is suited for connection to two different kinds of water faucets.

The threaded neck 7 confines a recess 8, which has a central bore hole 9, through which a threaded bolt 10 goes. The bore hole 9 consists of a bore hole section 11 on the inlet side, which is wider, and an adjacent, narrower bore hole section 12. In the wider bore hole section 11 lies the screw head 13, which is followed by a stepped cylindrical neck section 14 without threads. The neck section 14 is further followed by another stepped threaded section 15, which engages with the upper threaded section of a central bore hole 16 in the inner part 5 of the outlet part 3.

The inlet part 12 and the inner part 5 of the outlet part 3 each have plane end faces 17 and 18 which are facing each other parallel. In the assembled condition, the two end faces 17 and 18 rest against each other rotatably. Here, the threaded bolt 10 is seated with its neck section 14 on the end face 18 of the inner part 5. As the axial height of the neck section 14 is somewhat larger than the depth of the narrower bore hole section 12 in the inlet part 2, the outlet part 3 is rotatable relative to the inlet part 2.

At the inlet part 2, there is a projection 19 with a cylindrical inside surface 20 which protrudes beyond the end face 17 of the inlet part 2. The inner part 5 is defined by an outer cylinder surface 21, in which there is a circular groove, in which a sealing ring 22 engages. In the assembled condition of the adapter 1, the projection 19 at the inlet part 2 extends over the outer cylinder surface 21 at the inner part 5. The sealing ring is here in tight contact with the inside surface 20, so that the inlet and outlet parts 2 and 3 can rotate relative to each other, in sealed relationship.

The inlet part 2 has several off-center canals or bore holes 23 to 27 (FIG. 2) all of which join the recess 8 at the inlet side and which exit at the end face 17. Of the off-center bore holes 23 to 27, only the bore holes 23 and 27 are visible in FIG. 1. The bore hole 23 is somewhat wider than the bore holes 24 and 25 of equal diameter. The identically shaped bore holes 26 and 27 each consist on the exit side of a wider bore hole section 28 and 29, respectively, which is followed by a narrower bore hole section 30 and 31, respectively, adjacent to the recess 8 on the inlet side. Circular small valve disks 32, of which in FIG. 1 only the one valve disk 32 is visible in the bore hole 29, fit into the wider bore hole section 28 and 29. The valve disks 32 are arranged in the bore hole sections 28 and 29 so that they can easily move axially and radially in order to perform a valve flap function, and they are lapped at least on the side facing the end face 18.

In the inner part 5 of the outlet part 3, there are two canals or bore holes 33 and 34. The width of the bore hole 33 corresponds to the width of the bore hole 23 and the width of the bore hole 34 corresponds to the width of one of the two bore holes 24, 25. The bore hole 33 is brought through the inner part 5 in the axial direction. The bore hole 34 runs inward at an angle and joins the central bore hole 16, which ends in a coupling part 35 with an internal groove 36 for a sealing ring to be inserted. Into the coupling part can be inserted a plug part, known per se but not shown, to which a rubber tube or hose is connected which leads, for instance, to a mouth douche. Between the sleeve 4 and the protruding coupling 35, there is a space 37 into which a screening element or conventional aerator (not shown) could be inserted, if desired.

The bore hole 23 in the inlet part 2 serves to connect the recess 8 on the inlet side to the bore hole 33 in the outlet part 3, and the bore holes 24 and 25 in the inlet part 2 serve to connect the recess 8 to the bore hole 34 in the outlet part.

The outlet part 3 can be rotated by a certain angle of rotation relative to the inlet part 2 in both directions into two end positions. For this purpose, the projection or extension 19 at the insert part has a cutout 38 for forming rotation-limiting stops 39, 40 for a pin 41 in the sleeve 4 of the outlet part 3, which protrudes radially outward and extends up into the inner part 5.

In the one limiting-stop position shown in FIG. 1, the full cross section of the bore hole 23 is connected to the full cross section of the bore hole 33. At the same time, the valve disk 32 is located in the wider bore hole section 29 over the bore hole 34. The valve disk 32, which has a larger diameter than the bore hole 34, is pressed tightly here onto the end face 18 of the outlet part 3 by the water pressure from the inlet canal 8, for closing off the opening of the bore hole 34. Water from the inlet canal 8 thus flows through the canal 33 and, via the screening element 37 at the circumference of the central coupling part to the outside.

If the outlet part 3 is rotated from its one end position at the rotation-limiting stop 40, as shown in FIG. 1, in the direction toward the other rotation-limiting stop 39, into its other end position, then the valve disk 32 gets into the bore hole section 29 for releasing the bore hole 34 from its shut-off position. At the same time, the inlet of the bore hole 33 is shifted relative to the exit of the bore hole 23, whereby the free passage cross section between the bore holes 23 and 33 is throttled more and more, while the exit of the bore hole 25 shifts more and more over the entrance of the bore hole 34 and thereby increasingly opens up the passage cross section between the bore holes 25 and 34. In this manner, any intermediate position can be adjusted, in which the simultaneously released opening cross section between the bore holes 23 and 33 on the one hand, and the bore holes 25 and 34, on the other hand, can be adjusted in any desired opening ratio relative to each other. Thereby, the desired water pressure in the hose connected centrally to the adapter but not shown here, can be regulated continuously.

If the outlet part continues to be rotated in the direction toward the rotation-limiting stop 40, then the other valve disk 32, not visible in FIG. 1, in the bore hole section 28 comes to lie over the bore hole 33 to close the latter off increasingly, until it finally comes to lie completely over the bore hole 33 and the connection between the inlet canal 8 and the bore hole 33 is thus interrupted. Here, too, the diameter of the valve disk 32 is larger than the diameter of the opening of the bore hole 33 in the end face of the inner part 5. To the same extent as the inlet of the bore hole 33 is covered up more and more by the valve disk 32, the outlet of the bore hole 24 also shifts increasingly over the inlet of the bore hole 34. If the outlet part has been rotated up to the other rotation-limiting stop 40 relative to the inlet part, then the full opening cross section of the bore hole 24 in the inlet part 2 connects to the full opening cross section 34 in the outlet part, while, at the same time, the entrance of the bore hole 33 is tightly closed off under the pressure of the water acting on the valve disk 32 in the bore hole section 28. In an intermediate position, both bore holes 24 and 25 are connected to the bore hole 34 while the bore hole 33 is shut off, so that then the full water pressure from the water faucet acts on the appliance connected to the water hose, e.g., a mouth douche, if the water hose is connected to the coupling part 35 via a known coupling plug.

FIGS. 4 and 5 show outlet parts which are modified with respect to the outlet part 3 according to FIG. 1 and can be joined to the input part according to FIG. 1 to form an adapter according to the invention. Corresponding parts in FIGS. 1, 4 and 5 are therefore provided with the same reference symbols, differentiated by primes.

The outlet part 3' in FIG. 4 substantially differs from the outlet part 3 in FIG. 1 in that it is made of one piece and has a separate coupling part 35' which is connected to the bore hole 34', here extending in the axial direction, via a tap hole 42. The coupling member 35' is joined to the connecting part 3' via a bushing 42'. The end of the outlet part 3' on the outlet side is designed here with a threaded neck 43 with external threads for screwing-on a known aerator. Instead of the external threads, an internal thread may be provided into which an aerator may be screwed. The end on the outlet or exit side may also be designed in accordance with FIG. 5 for inserting an aerator.

FIG. 5 shows a further outlet part 3', which is likewise made of one piece and has on the outlet side a recess 44 providing a space 47 into which an aerator may be inserted. To connect this aerator 47 tightly to the bore hole 23", a sealing ring 46 is disposed in the recess 44. The aerator 47 is held in the recess 44 by a snap ring 48, which engages with a groove 45 at the outlet or exit end of the recess 44. Instead of the snap ring 48, a correspondingly flat mounting screw ring with external threads may be provided which engages with an internal thread at the exit end of the recess 44.

Contrary to FIG. 4, the separate coupling member 35" in FIG. 5 is an integral piece with the outlet part 3". The bore hole 34" runs outward at an angle for connecting to the coupling member 35". This connecting part 3" is preferably made of plastic, the outlet part having an oval, tear-like shape. A bushing 46 of metal (brass) is pressed into the end on the outlet or exit side of the coupler opening, to which a coupling plug, not shown, can be coupled. The bushing 46 can also be placed in advance into the mold for making the connecting part 3" by injection molding.

The coupling bushing 46 has an internal groove 49 corresponding to the grooves 36 and 36' in FIGS. 1 and 4. If a corresponding groove can be made in the connecting part 3" as such by injection-molding techniques, such a bushing 46 becomes superfluous. It is important that the tolerances of the grooves 36, 36' and 49 are sufficiently narrow, so that the coupling plugs for connecting the hoses can be connected tightly. Instead of using a bushing 46, a groove 49 can also be cut into the finished outlet part 3" of plastic by means of a tool.

The thread in the central hole 16" is cut in the finished outlet part 3". However, a bushing 52 of metal corresponding to the bushing 46 can also be used, which has an internal thread for engaging the threaded bolt 10, whereby the bushing is pressed into a central recess of the finished connecting part 3" or is placed in advance into the mold for making the outlet part 3" as an injection molding part. The bushing 52 is shown in FIG. 5 with dashed lines as a variant.

The hole 34" need not be made as an oblique hole. As indicated as a variant by dashed lines, the hole 34" can also run in the axial direction until it joins a likewise dashed transversal hole 50 which is closed tight to the outside by a plug or stopper 51. It is a production question whether the outlet part 3" can be made preferably of plastic with a hole 34 as per the solid lines or perhaps cheaper with holes along the dashed lines. The same is true for a groove 49 which is cut later into the finished outlet part 3" and the metal bushing 46 with a corresponding groove 49 as a variant, or the thread of the central bore hole 16" cut later into the finished outlet part 3" and the metal bushing 52 in a corresponding internal thread as a variant.

The aerator 47 inserted into the recess 44 need not be held to the outlet part 3" by a snap ring 48. Instead, a setscrew 53, which can be screwed into the outlet part from the outside and is shown here dashed as a variant and which holds the aerator 47 in the recess, may also be provided. As a further variant for holding an aerator in the recess 44, the latter may have an internal thread for screwing-in an aerator with an external thread. It is important that the aerator can be inserted or screwed easily into the recess 44 and removed again, and that the aerator can always be connected tightly to the hole 23".

It is clear that the holes, designated here as 16", 23" and 34", are designed, if the outlet part 3" is designed as an injection molding of plastic, at least in part as recesses or breakthroughs or canals, which are not drilled out. This applies in particular to the bores 23" and 16".

If the inlet part as per FIG. 1 is to be provided with an internal and an external connecting thread for different water faucets, it is advantageous that it be made of metal (e.g., brass), which can be combined with an outlet part 3" as per FIG. 5 of plastic. If the inlet part 2 is equipped only with one connecting thread as per FIG. 1, it can be made, like the outlet part 3" as per FIG. 5, of plastic, so that then the entire adapter is made of plastic. In the case of the outlet part 3 as per FIG. 1, at least the outer sleeve 4 may be made of plastic.

Although the invention has been described with reference to specific example embodiments, it will be appreciated, that it is intended to cover all modifications and equivalents within the scope of the appended claims.

We claim:

1. An adapter for connection to an outflow end of a liquid faucet, comprising a central axis, an inlet part and an outlet part disposed in axial alignment with said inlet part relative to said central axis, valve means operatively disposed between said inlet part and said outlet part for rotation about said central axis, said inlet part comprising at one side thereof means for connection to said outflow end of the liquid faucet, said inlet part further comprising at the other side thereof a first plane end face (17) and a plurality of first flow channel means (23 to 27) extending through said inlet part from said one side to said other side of said inlet part, said outlet part comprising a second plane end face (18) facing said first plane end face (17) of said inlet part, and exit port means substantially opposite said second plane end face, said outlet part further comprising a plurality of second flow channel means extending from said second plane end face to said exit port means, means operatively connecting said inlet part and said outlet part to each other for rotating the outlet part relative to the inlet part, said valve means further comprising valve sealing body means operatively located between said inlet part and said outlet part, said valve sealing body means being subject to the liquid pressure from said faucet through at least one of said first flow channel means whereby said valve sealing body means control the size of the cross-sectional flow area between said at least one first flow channel means and a respective one of said second flow channel means in response to rotation of said outlet part relative to said inlet part, while simultaneously providing the necessary sealing and whereby the ratio of open cross-sectional flow area to closed cross-sectional area is continuously adjustable by said rotation.

2. The adapter of claim 1, wherein said plurality of second flow channel means comprise first and second flow channel members which are separated from each other in said outlet part, said first and second flow channel members opening into said second plane end face of said outlet part, said exit port means comprising first and second exit ports, said first flow channel member leading to said first exit port, said second flow channel member leading to said second exit port, said inlet part having recesses in said first plane end face, said first flow channel means opening into a respective one of said recesses, said valve body means comprising disk means located in said recess means, said disk means having a diameter larger than the diameter of said second channel means, said connecting means including means for limiting the angle of rotation of said outlet part relative to said inlet part, whereby in a first position of rotation one of the first and second flow channel members of the outlet part is closed off by the respective valve disk means due to the liquid pressure loading of said respective valve disk means, and whereby the other of said first and second flow channel members of the outlet part is operatively connected to at least one of said first flow channel means in said inlet part for liquid flow therethrough, whereas in a second position of rotation of the outlet part relative to the inlet part the closed and open condition is reversed, said valve body disk means further providing for a partial closing of the respective flow channel means when the inlet part and the outlet part take up positions intermediate said first and second rotational positions.

3. The adapter of claim 2, wherein said means for operatively connecting said inlet part and said outlet part to each other comprise screw means extending along said central axis.

4. The adapter of claim 1, wherein said connecting means comprise a central opening in said inlet part with a wider portion (11) adjacent to said one side and a narrower portion (12) toward said other side, said screw means (10) extending through the opening and having a screw head (13) resting in the wider portion, said screw further having a stepped shank section extending with play through said narrower portion (12), said screw means further having a threaded section (15), said outlet part having a central bore hole (15') into which said threaded screw section extends, whereby said shank section (14) is resting on the second plane end face (18) of the outlet part (3), said shank section having an axial height somewhat larger than the axial depth of said narrower opening portion (12) in the inlet part (2).

5. The adapter of claim 1, wherein said inlet part (2) and said outlet part (3) each comprises a respective cylindrical section which engage each other, said adapter further comprising sealing ring means (22) arranged between said cylindrical sections (20, 21).

6. The adapter of claim 1, wherein said exit port means comprise an outlet opening (35) including coupling means adapted for receiving a coupling plug connected to a hose.

7. The adapter of claim 6, wherein said coupling means are disposed centrally in said exit port means of the outlet part (3).

8. The adapter of claim 6, wherein the coupling means are disposed outside of said exit port means.

9. The adapter of claim 1, wherein said outlet part (3') is a turned part which has, opposite said second plane end face (18) a wide cylindrical recess for receiving or connecting an aerator, said second flow channel means comprising one channel connecting said recess to said second plane end face (18), which faces said first plane end face, said connecting means comprising screw means (10) and a central blind hole (16') with an internal threading in said second plane end face for engaging the screw means (10), said second flow channel means comprising a further channel (34') and a transversal passage (42) open to the outside as well as a tubular body comprising a coupling section.

10. The adapter of claim 1, wherein said outlet part has adjacent said second plane face (18) a cylindrical section which surrounds the second plane face (18), said cylindrical section having a circular groove (21), sealing ring means accommodated in said groove, cylindrical recess means (44) provided for an aerator in said outlet part adjacent said exit port means, further cylindrical recess means smaller than said first mentioned cylindrical recess means and separated from the latter cylindrical recess means, for forming a coupling part which forms a unit with the outlet part, said second flow channel means comprising one channel extending from the second plane end face (18) which opens into the larger cylindrical recess, and a second channel (34") which connects to the smaller cylindrical recess, said connecting means comprising a central blind hole (16") in said second plane end face with an internal threading and screw means (10) engaging said threading.

11. An adapter for connection to a liquid faucet, comprising an inlet part (2) and an outlet part (3) disposed axially aligned to the inlet part, said inlet part (2) comprising on the faucet side a recess (8) adapted to be tightly connected to the outflow end of the faucet, said inlet part (2) having on the exit side a plane end face (17) into which several channels (23 to 27) open which are connected to the recess (8), said outlet part having on the inlet side a plane end face (18) into which several channels (33, 34) open, each of which is connected to an outflow opening, said inlet part (2) comprising a central opening with a section (11) wider on the inlet side and a narrower section (12) following on the outlet side; and screw means (10) extending through the opening, said screw means having a screw head (13) resting in the wider section of the inlet part, said screw head (13) having a stepped shank section (14) below the screw head which extends with play through the narrower section (12), said stepped shank section (14) being followed by a stepped threaded section (15) which engages in a central bore hole (15') in the end face of the outlet part (3), said shank section (14) resting on the plane end face (18) of the outlet part (3), the axial height of the neck section being somewhat larger than the axial depth of the narrower hole section (12) in the inlet part (2).

12. The adapter of claim 11, wherein the inlet part (2) and the outlet part (3) engage each other with cylindrical sections (20, 21) and wherein a sealing ring (22) is arranged between the cylindrical sections (20, 21).

13. The adapter of claim 11, wherein the outlet part has on the inlet side a cylindrical section which surrounds the plane end face (18), said cylindrical section having a circular groove (21) for accommodating a sealing ring (22), and wherein a larger cylindrical recess (44) is provided for an aerator on the exit side, and a smaller, separate cylindrical recess forms a coupling part which forms a unit with the outlet part, wherein a first channel extends from the end face (18) to said larger cylindrical recess, whereas a second channel (34") connects to the smaller cylindrical recess, and wherein the central blind hole (16") in the end face, has an internal threading for screw means (10).

14. An adapter for connection to a liquid faucet, comprising an inlet part (2), an outlet part (3) disposed coaxially to the inlet part, said inlet part (2) having on the faucet side a recess (8) which can be tightly connected to the outflow end of the faucet, said inlet part (2) having on the exit side a plane end face (17) and several channels (23 to 27) opening into said end face, said several channels being connected to the recess (8), said outlet part comprising on the inlet side a plane end face (18) and several further channels (33, 34) opening into the respective end face, said outlet part further comprising outflow openings to which the respective further channel is connected, said inlet part (2) and said outlet part (3) further comprising respective, engaging cylindrical sections (20, 21), and wherein a sealing ring (22) is arranged between the cylindrical sections (20, 21), said adapter further comprising valve sealing body means operatively located between said inlet part and said outlet part in the area of said engaging cylindrical sections, wherein said cylindrical section of the outlet part surrounds the plane end face (18) of the outlet part, said cylindrical section having a circular groove (21) for accommodating said sealing ring (22), said outlet part comprising a larger cylindrical recess (44) for an aerator, and a smaller cylindrical recess separated from the larger cylindrical recess constituting a coupling which forms a unit with the outlet part, a first channel (33") extending from the end face (18) to the larger cylindrical recess in said outlet part, and a second channel (34") connecting to the smaller cylindrical recess, said outlet part further comprising in the end face, a central blind hold (16") with an internal thread for connecting screw means.

* * * * *